(12) United States Patent
Boillot et al.

(10) Patent No.: US 9,141,254 B2
(45) Date of Patent: Sep. 22, 2015

(54) NAVIGATION SYSTEM AND USER INTERFACE FOR DIRECTING A CONTROL ACTION

(75) Inventors: Marc Boillot, Plantation, FL (US); Jason McIntosh, Sugar Hill, GA (US)

(73) Assignee: ORTHOSENSOR INC, Dania Beach, FL (US)

( * ) Notice: Subject to any disclaimer, the term of this patent is extended or adjusted under 35 U.S.C. 154(b) by 791 days.

(21) Appl. No.: 12/900,878

(22) Filed: Oct. 8, 2010

(65) Prior Publication Data

US 2011/0029913 A1 Feb. 3, 2011

Related U.S. Application Data

(63) Continuation-in-part of application No. 11/559,295, filed on Nov. 13, 2006, now Pat. No. 7,847,787.

(60) Provisional application No. 60/735,327, filed on Nov. 12, 2005.

(51) Int. Cl.
*G09G 5/00* (2006.01)
*G06F 3/0481* (2013.01)
*A61B 19/00* (2006.01)
*G06F 3/01* (2006.01)
*G06F 3/0346* (2013.01)
*A61B 17/00* (2006.01)
*G06F 19/00* (2011.01)

(52) U.S. Cl.
CPC .......... *G06F 3/0481* (2013.01); *A61B 19/5244* (2013.01); *A61B 19/56* (2013.01); *G06F 3/011* (2013.01); *G06F 3/0346* (2013.01); *A61B 2017/00207* (2013.01); *A61B 2017/00221* (2013.01); *A61B 2017/00734* (2013.01); *A61B 2019/5248* (2013.01); *A61B 2019/5263* (2013.01); *A61B 2019/5268* (2013.01); *A61B 2019/564* (2013.01); *G06F 19/3406* (2013.01)

(58) Field of Classification Search
CPC ..... G06F 3/0481; G06F 3/011; G06F 3/0346; G06F 19/3406; A61B 19/5244; A61B 19/56; A61B 2017/00734; A61B 2017/00221; A61B 2017/00207; A61B 2019/5268; A61B 2019/5248; A61B 2019/5263; A61B 2019/564
USPC .......................... 345/156–184; 702/150–153; 715/862–863
See application file for complete search history.

(56) References Cited

U.S. PATENT DOCUMENTS

| | | | | |
|---|---|---|---|---|
| 6,167,296 | A * | 12/2000 | Shahidi | 600/427 |
| 6,669,635 | B2 | 12/2003 | Kessman et al. | |
| 7,302,288 | B1 | 11/2007 | Schellenberg | |
| 7,394,346 | B2 * | 7/2008 | Bodin | 340/5.51 |
| 7,458,977 | B2 * | 12/2008 | McGinley et al. | 606/130 |
| 7,620,316 | B2 * | 11/2009 | Boillot | 396/429 |
| 7,643,867 | B2 | 1/2010 | Solar et al. | |
| 7,698,002 | B2 * | 4/2010 | Music et al. | 700/17 |

(Continued)

*Primary Examiner* — Rodney Amadiz (57) ABSTRACT

A navigation system is provided to direct control of a user interface work-flow during a procedure. Such a need can arise in sterile environments were touchless interaction is preferable over physical contact. The system includes a wand and receiver for controlling a pagination and parameter entry of the work-flow, a processor to compare wand movement profiles, a clock for limiting a time window between the comparison, and a controller for activating a user interface control in the workflow when a wand movement profile or gesture is recognized. The comparison can be based on the wand's direction, orientation and movement to and from various locations. Other embodiments are disclosed.

21 Claims, 5 Drawing Sheets

(56) References Cited

U.S. PATENT DOCUMENTS

| | | | |
|---|---|---|---|
| 7,750,891 B2 | 7/2010 | Stephanick et al. | |
| 7,768,498 B2 | 8/2010 | Wey | |
| 7,834,847 B2 * | 11/2010 | Boillot et al. | 345/156 |
| 7,834,850 B2 * | 11/2010 | Boillot et al. | 345/158 |
| 8,570,274 B1 * | 10/2013 | McIntosh et al. | 345/158 |
| 8,814,810 B2 * | 8/2014 | Roche et al. | 600/587 |
| 8,864,686 B2 * | 10/2014 | Roche et al. | 600/587 |
| 9,011,448 B2 * | 4/2015 | Roche et al. | 606/86 R |
| 2002/0033803 A1 * | 3/2002 | Holzrichter et al. | 345/158 |
| 2004/0125081 A1 * | 7/2004 | Hayakawa | 345/156 |
| 2007/0129629 A1 * | 6/2007 | Beauregard et al. | 600/424 |
| 2009/0167719 A1 * | 7/2009 | Woolley | 345/174 |
| 2009/0215534 A1 | 8/2009 | Wilson et al. | |
| 2010/0151946 A1 * | 6/2010 | Wilson et al. | 463/36 |
| 2010/0201808 A1 | 8/2010 | Hsu | |
| 2010/0210939 A1 | 8/2010 | Hartmann et al. | |
| 2010/0249817 A1 | 9/2010 | Mark | |
| 2011/0102455 A1 * | 5/2011 | Temple | 345/619 |
| 2011/0275957 A1 * | 11/2011 | Bhandari | 600/595 |

\* cited by examiner

NAVIGATION SYSTEM AND USER INTERFACE FOR DIRECTING A CONTROL ACTION

CROSS-REFERENCE TO RELATED APPLICATION

This application is a Continuation-In-Part of U.S. patent application Ser. No. 11/559,295 filed on Nov. 13, 2006 claiming the priority benefit of U.S. Provisional Patent Application No. 60/735,327 filed on Nov. 12, 2005, the entire contents of which are hereby incorporated by reference. This application also claims priority benefit to U.S. patent application Ser. No. 12/723,486 filed on Mar. 12, 2010 claiming the priority benefit of U.S. Provisional Patent Application No. 61/159,793 filed on Mar. 12, 2009, the entire contents of which are hereby incorporated by reference.

BACKGROUND

1. Field

The present embodiments of the invention generally relate to the field of user interfaces, and more particularly to input pointing devices.

2. Introduction

Navigation systems and other sensing technologies generally include a display. Interaction with the display can occur via mouse, keyboard or touch screen. There are cases however when the display or its control devices are not directly accessible and a touchless interaction is preferable.

BRIEF DESCRIPTION OF THE DRAWINGS

FIG. 4B is an exemplary illustration for vertical workflow calibration in accordance with one embodiment;

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward.

Broadly stated, a system and method is provided to direct control of a user interface workflow via touchless navigation. Such need arises in situations were touchless interaction is preferable over a touch based approach, for example, in a sterile environment, such as an operating room. In such case, a touchscreen may not be accessible, or, if present, requires the assistance of a technical specialist outside the sterile field. The navigation system herein permits touchless user interface control via a wand which is concurrently used during a surgical procedure in the sterile field. The wand serves as a navigation instrument during the procedure, and dually for interacting with the user interface workflow during the procedure. The receiver is a navigation instrument also used during the surgery, and dually serves to convey user interface directives to a remote system presenting the user interface workflow.

Figure 1:
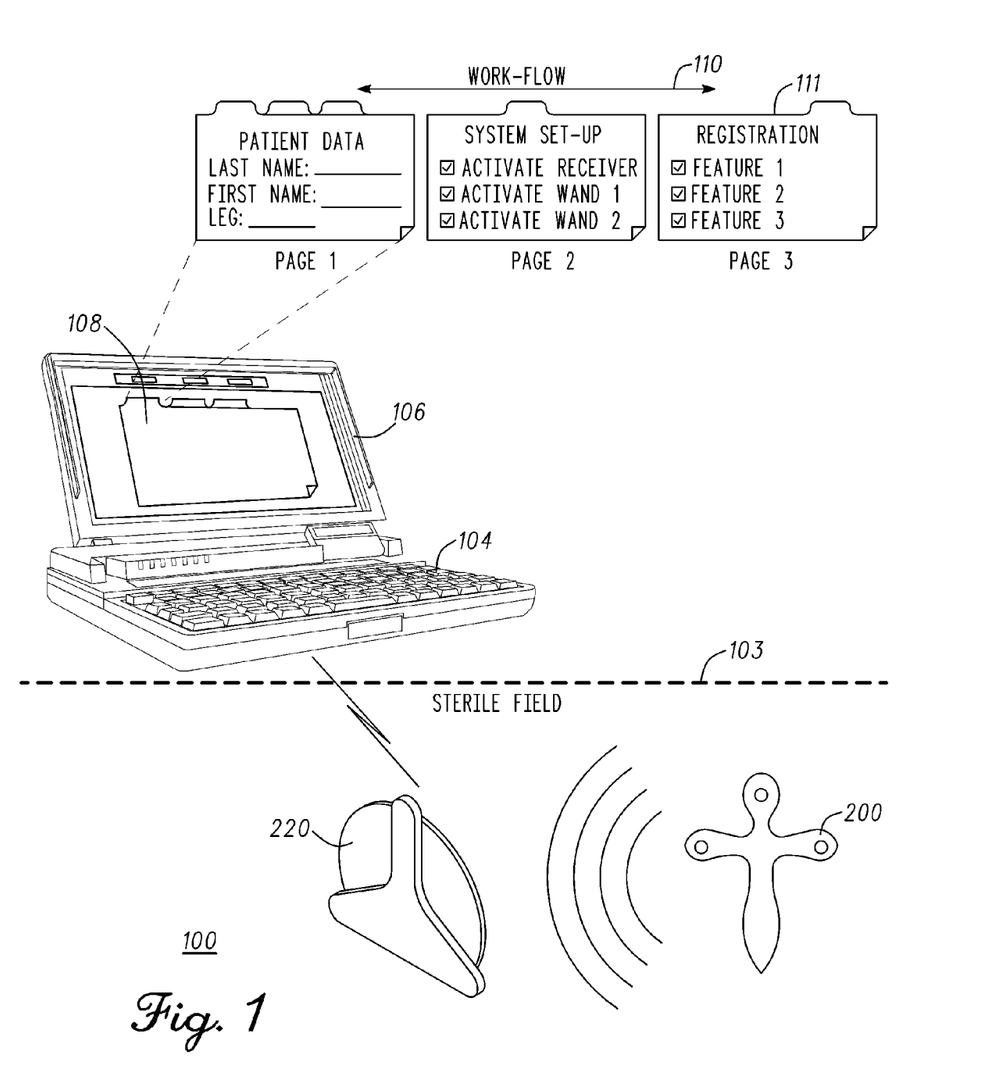
FIG. 1 is a navigation system hosting a user interface workflow in accordance with one embodiment.

Referring to FIG. 1, a navigation system 100 for directing a user interface control action in an orthopedic application is shown according to one embodiment. The navigation system 100 includes a wand 200 and a receiver 220 that can be used within a sterile field 103; an area designated within an operating room where all equipment and instruments are sterile. The two devices are hand-held navigation instruments that identify anatomical features of interest and record their location and position. On example of wand registration of points of interest for anatomical alignment and positional measurements during a surgical procedure is disclosed in U.S. patent application Ser. No. 12/764,072 entitled "Method and System for Positional Measurement using Ultrasonic Sensing" the entire contents of which are hereby incorporated by reference. The embodiments herein are not however limited to medical procedures; the reference disclosed above is an example.

The wand 200 and receiver 220 directly communicate with one another via a wired or wireless connection. The receiver 220 communicates via a wireless connection to the remote system 104 which can include the display 106. The remote system 104 can be a computer, laptop, or a cell phone or combination thereof; it is not limited to mobile devices. The remote system 104 hosts the Graphical User Interface (GUI) 108 which presents the workflow 110 associated with the navigated procedure. The GUI 108 can be a local application resident on the remote system 106, an on-line application provided by an Internet Service Provider or cloud computing system, a cable or internet-TV provider, or a down-loadable application over the air (e.g., cellular infrastructure, telecom, etc.).

In addition to procedural capabilities, the wand 200 and receiver 220 provide supplemental control to the Graphical User Interface (GUI) 108 presenting with the work flow 110 of the surgical procedure, although, any type of procedure is herein contemplated. This permits the user to handle the wand 200 to control the user interface workflow 110 of the procedure without contacting the display 106, and can dually serves as a surgical tool in the course of a navigated procedure. That is, the wand and the receiver are instruments that can register anatomical points of interest and report anatomical alignment and positional measurements of the registered points during the procedure but are also used intermittently for touchless user interface control of the GUI 108 during the procedure.

The work-flow 110 includes a plurality of pages 111 that are presented during handling of the wand 200. Each page my be a separate screen, tab or view, but is not limited to these. The pages 111 can be staged or staggered over time (paginated) and according to certain workflow states of the navigation system 100. As an example, a first state may correspond to information or parameter entry. For instance, the user can enter user interface parameters into a page via wand movements, or wand gestures. A second state may correspond to a page transition, for example, to a next page (or previous page) via a pattern wand movement as will be explained ahead. The GUI 108 controls a pagination of the workflow 110 via user directives from the receiver 220 which itself interprets the wand 200 movement conveying the underlying user interface control. The pagination can occur as a result of a state change, for example, completing all entries on a page, or in response to a wand gesture, for example, a directed wave.

Figure 2A:
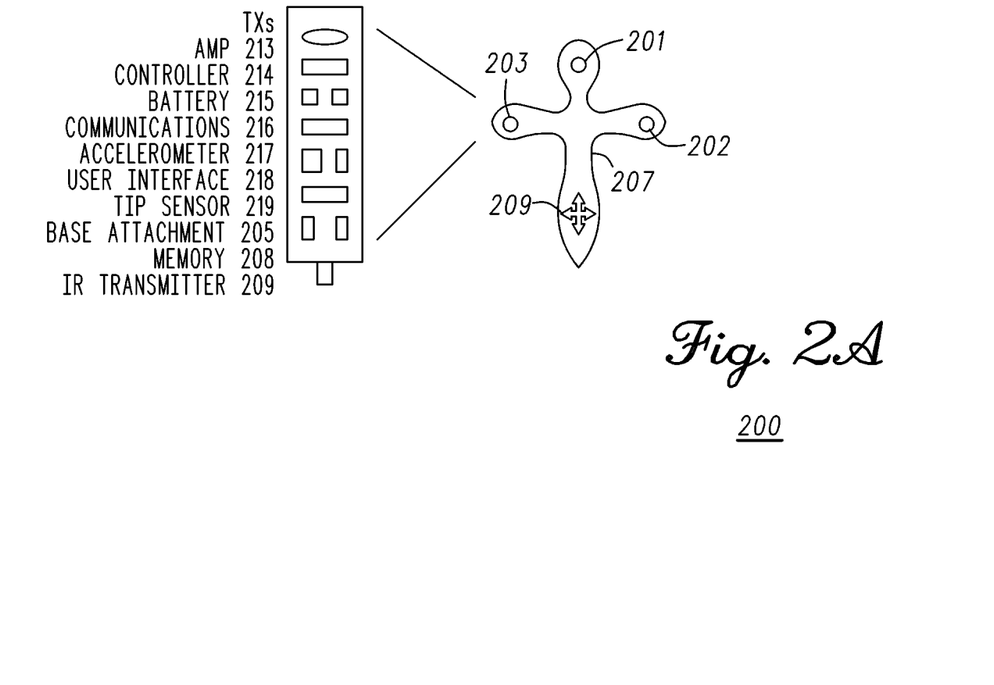
FIG. 2A is a wand for directing workflow commands to the user interface in accordance with one embodiment.

FIG. 2A shows one exemplary embodiment of the wand 200. The wand 200 includes sensors 201-203 and a wand tip 207. The sensors can be ultrasonic transducers, Micro Electro Mechanical Element (MEMS) microphones, electromagnets, optical elements (e.g., infrared, laser), metallic objects or other transducers for converting or conveying a physical movement to an electric signal such as a voltage or current. They may be active elements in that they are self powered to transmit signals, or passive elements in that they are reflective or exhibit detectable magnetic properties.

In a preferred embodiment, the wand 200 comprises three ultrasonic transmitters 201-203 for each transmitting ultrasonic signals through the air, an electronic circuit (or controller) 214 for generating driver signals to the three ultrasonic transmitters 201-203 for generating the ultrasonic signals, an user interface 218 (e.g., button) that receives user input for performing short range positional measurement and alignment determination, a communications port 216 for relaying the user input and receiving timing information to control the electronic circuit 214, and a battery 215 for powering the electronic circuit 215 and associated electronics on the wand 200. The wand 200 may contain more or less than the number of components shown; certain component functionalities may be shared as integrated devices.

Additional transmitter sensors can be included to provide an over-determined system for three-dimensional sensing. As one example, each ultrasonic transducer can perform separate transmit and receive functions. One such example of an ultrasonic sensor is disclosed in U.S. patent application Ser. No. 11/562,410 filed Nov. 13, 2006 the entire contents of which are hereby incorporated by reference. The ultrasonic sensors can transmit pulse shaped waveforms in accordance with physical characteristics of a customized transducer for constructing and shaping waveforms.

The wand tip 207 identifies points of interest on a structure, for example, a rod, bone, instrument or jig in three-dimensional space but is not limited to these. The tip does not require sensors since its spatial location in three-dimensional space is established by the three ultrasonic transmitters 201-203 arranged at the cross ends. However, a sensor element can be integrated on the tip 207 to provide ultrasound capabilities (e.g., structure boundaries, depth, etc.) or contact based sensing. In such case, the tip 207 can be touch sensitive to registers points responsive to a physical action, for example, touching the tip to an anatomical or structural location. The tip can comprise a mechanical or actuated spring assembly for such purpose. In another arrangement it includes a capacitive touch tip or electrostatic assembly for registering touch. The wand tip 207 can include interchangeable, detachable or multi-headed stylus tips for permitting the wand tip to identify anatomical features while the transmitters 201-203 remain in line-of-sight with the ultrasonic receiver 220 (see FIG. 1). These stylus tips may be right angled, curved, or otherwise contoured in fashion of a pick to point to difficult to touch locations. This permits the wand to be held in the hand to identify via the tip 207, points of interest such as (anatomical) features on the structure, bone or jig.

The user interface 218 can include one or more buttons to permit handheld operation and use (e.g., on/off/reset button) and illumination elements to provide visual feedback. In one arrangement, a 5 state navigation press button 209 can communicate directives to further control or complement the user interface. It can be ergonomically located on a side of the wand to permit single handed use. The wand 200 may further include a haptic module with the user interface 218. As an example, the haptic module may change (increase/decrease) vibration to signal improper or proper operation. The wand 200 includes material coverings for the transmitters 201-202 that are transparent to sound (e.g., ultrasound) and light (e.g., infrared) yet impervious to biological material such as water, blood or tissue. In one arrangement, a clear plastic membrane (or mesh) is stretched taught; it can vibrate under resonance with a transmitted frequency. The battery 215 can be charged via wireless energy charging (e.g., magnetic induction coils and super capacitors).

The wand 200 can include a base attachment mechanism 205 for coupling to a structure, bone or a jig. As one example, the mechanism can be a magnetic assembly with a fixed insert (e.g., square post head) to permit temporary detachment. As another example, it can be a magnetic ball and joint socket with latched increments. As yet another example, it can be a screw post o pin to an orthopedic screw. Other embodiments may permit sliding, translation, rotation, angling and lock-in attachment and release, and coupling to standard cutting jigs by way of existing notches, ridges or holes.

Figure 2B:
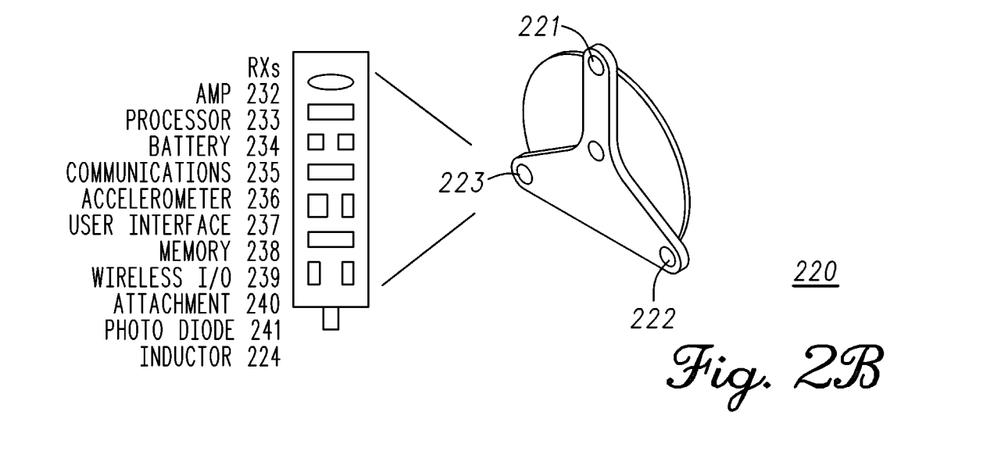
FIG. 2B is a receiver for interpreting wand movement and gestures in accordance with one embodiment.

The wand 200 can further include an amplifier 213 and the accelerometer 217. The amplifier enhances the signal to noise ratio of transmitted or received signals. The accelerometer 217 identifies 3 and 6 axis tilt during motion and while stationary. The communications module 216 may include components (e.g., synchronous clocks, radio frequency 'RF' pulses, infrared 'IR' pulses, optical/acoustic pulse) for signaling to the receiver 220 (FIG. 2B). The controller 214, can include a counter, a clock, or other analog or digital logic for controlling transmit and receive synchronization and sequencing of the sensor signals, accelerometer information, and other component data or status. The battery 215 powers the respective circuit logic and components. The infrared transmitter 209 pulses an infrared timing signal that can be synchronized with the transmitting of the ultrasonic signals (to the ultrasonic receiver).

The controller 214 can utilize computing technologies such as a microprocessor (uP) and/or digital signal processor (DSP) with associated storage memory 108 such a Flash, ROM, RAM, SRAM, DRAM or other like technologies for controlling operations of the aforementioned components of the device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm. The controller can be an embedded platform running one or more modules of an operating system (OS). In one arrangement, the storage memory may store one or more sets of instructions (e.g., software) embodying any one or more of the methodologies or functions described herein.

FIG. 2B shows the receiver 220 according to one embodiment. The receiver 220 comprises a processor 233 for generating timing information, registering a pointing location of the wand 200 responsive to the user input, and determining short range positional measurement and alignment from three or more pointing locations of the wand 200 with respect to the ultrasonic receiver 220. It includes a communications interface 235 for transmitting the timing information to the wand 200 that in response transmits the first, second and third ultrasonic signals. The ultrasonic signals can be pulse shaped signals generated from a combination of amplitude modulation, frequency modulation, and phase modulation. Three microphones 221-223 each receive the first, second and third pulse shaped signals transmitted through the air. The memory 238 stores the first, second and third ultrasonics signals and can produce a history of ultrasonic signals or processed signals. It can also store wand tip positions, for example, responsive to a user pressing the button to register a location. The wireless communication interface (Input/Output) 239 wirelessly conveys the positional information and the short range alignment of the three or more pointing locations to a remote system. The remote system can be a computer, laptop or mobile device that displays the positional information and alignment information in real-time as described ahead. The battery powers the processor 233 and associated electronics on the ultrasonic receiver 220. The ultrasonic receiver 200 may contain more or less than the number of components shown; certain component functionalities may be shared or therein integrated.

Additional ultrasonic sensors can be included to provide an over-determined system for three-dimensional sensing. The ultrasonic sensors can be MEMS microphones, ultrasonic receivers, ultrasonic transmitters or combination thereof. As one example, each ultrasonic transducer can perform separate transmit and receive functions. One such example of an ultrasonic sensor is disclosed in U.S. patent application Ser. No. 11/683,410 entitled "Method and Device for Three-Dimensional Sensing" the entire contents of which are hereby incorporated by reference. The ultrasonic receiver 220 can also include an attachment mechanism 240 for coupling to bone or a jig. As one example, the mechanism 240 can be a magnetic assembly with a fixed insert (e.g., square post head) to permit temporary detachment. As another example, it can be a magnetic ball and joint socket with latched increments.

The receiver 220 can further include an amplifier 232, the communications module 235, an accelerometer, and processor 233. The amplifier 232 enhances the signal to noise of transmitted or received signals. The processor 233 can include a controller, counter, a clock, and other analog or digital logic for controlling transmit and receive synchronization and sequencing of the sensor signals, accelerometer information, and other component data or status. The accelerometer 236 identifies axial tilt (e.g., 3/6 axis) during motion and while stationary. The battery 234 powers the respective circuit logic and components. The ultrasonic receiver includes a photo diode 241 for detecting the infrared signal and establishing a transmit time of the ultrasonic signals to permit wireless infrared communication with the wand.

The communications module 235 can include components (e.g., synchronous clocks, radio frequency 'RF' pulses, infrared 'IR' pulses, optical/acoustic pulse) for local signaling (to wand 102). It can also include network and data components (e.g., Bluetooth, ZigBee, Wi-Fi, GPSK, FSK, USB, RS232, IR, etc.) for wireless communications with a remote device (e.g., laptop, computer, etc.). Although external communication via the network and data components is herein contemplate, it should be noted that the ultrasonic receiver 220 can include a user interface 237 to permit standalone operation. As one example, it can include 3 LED lights 224 to show three or more wand tip pointing location alignment status. The user interface 237 may also include a touch screen or other interface display with its own GUI for reporting positional information and alignment.

The processor 233 can utilize computing technologies such as a microprocessor (uP) and/or digital signal processor (DSP) with associated storage memory 108 such a Flash, ROM, RAM, SRAM, DRAM or other like technologies for controlling operations of the aforementioned components of the terminal device. The instructions may also reside, completely or at least partially, within other memory, and/or a processor during execution thereof by another processor or computer system. An Input/Output port permits portable exchange of information or data for example by way of Universal Serial Bus (USB). The electronic circuitry of the controller can comprise one or more Application Specific Integrated Circuit (ASIC) chips or Field Programmable Gate Arrays (FPGAs), for example, specific to a core signal processing algorithm or control logic. The processor can be an embedded platform running one or more modules of an operating system (OS). In one arrangement, the storage memory 238 may store one or more sets of instructions (e.g., software) embodying any one or more of the methodologies or functions described herein.

Figure 3:
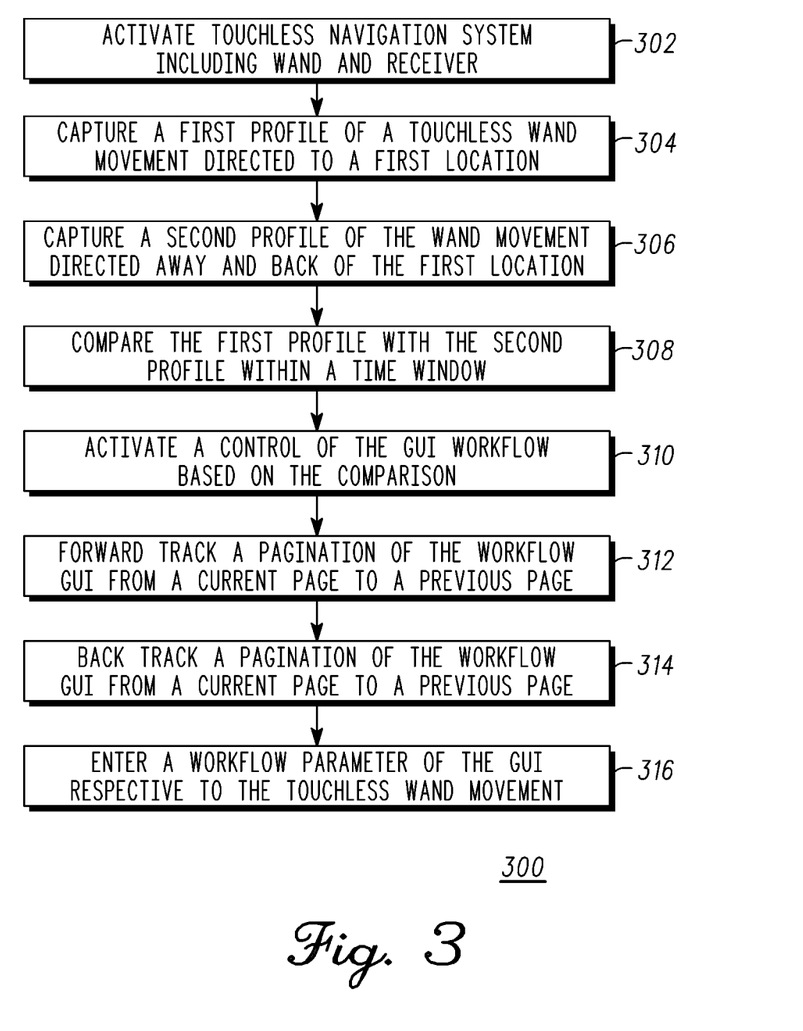
FIG. 3 is a method for virtual navigation of a user interface workflow in accordance with one embodiment.

Referring to FIG. 3, an exemplary method 300 for virtual navigation of a user interface workflow is shown according to one embodiment for example, in a sterile field. When describing the method 300, reference will be made to FIGS. 1, 2A, 2B, 4A, 4B, 5A and 5B, although the method 300 can be practiced in any other suitable system or device. Moreover, the steps of the method 300 are not limited to the particular order in which they are presented in FIG. 3. The method can also have a greater number of steps or a fewer number of steps than those shown.

The method 300 can start in a state where the remote system 104 (see FIG. 1) is turned on, the GUI 108 displays the workflow 110, and the patient's information has been entered (see "Page 1"). It can exhibit an acknowledgement behavior when a touchless wand movement is detected that is a visual cue. It is touchless in that the wand does not touch the display. At step 302, the wand 200 and receiver 220 of the navigation system 100 are activated. Each device is turned on via a button press. U.S. patent application Ser. No. 12/900,662 entitled "Navigation Device Providing Sensory Feedback" filed Oct. 8, 2010 discloses certain principles of operation employed herein; the entire contents of which are hereby incorporated by reference.

Referring to FIG. 1, this brings up "Page 2" of the workflow 110—the "System Set-up" page. The activation can occur within or outside the sterile field 103 depending on the workflow and customization. Each device reports its activation status locally (e.g., blinking green LED), or conveys status to the GUI 108 to show activation (e.g., icon activity) with the remote system 104. This step can further include a calibration step, or set-up, that synchronizes a timing of the devices and validates positional accuracy and operation. A further step can coordinate communication with remote system 104 for initializing the GUI 108.

The user then holds the wand 200, and moves it towards the receiver 220 (<10 cm), or any other predetermined location, while pressing the wand button to signal the start of the procedure. The navigation system 100 recognizes this directive as a command to commence the workflow 110 with touchless wand control. Referring back to FIG. 1, the GUI 108 paginates forward to "Page 3"—the "Registration" page of the work flow 110. The user then holds and moves the wand 200 in front of the receiver 220 to commence and visualize positional tracking on the GUI 108 for registration. Notably, the workflow 110 shown in FIG. 1 with corresponding pages 111 is merely one example of a workflow. Other pages can provide further information that are herein contemplated; the workflow is not limited to only the pages shown.

Continuing with method 300, the workflow 110 at "Page 3" prompts the user to identify feature 1 (see FIG. 1; a parameter entry) with the wand 200, and then waits for user-input. The user positions the wand tip 207 on feature 1 during the procedure and presses the wand button to register that feature. Upon registration and visual acknowledgement, the GUI proceeds to prompt the user to register feature 2. One example of providing visual feedback with touchless sensing applications is disclosed in U.S. patent application Ser. No. 11/562, 413 entitled "Providing Sensory Feedback" filed Nov. 21, 2006 the entire contents of which are hereby incorporated by reference The method 300 can continue for each "feature" of the parameter entry identified on the page. If however, the user reconsiders updating or reregistering feature 1, the user can hold the wand up, briefly pause, and then direct the wand 200 to a side, such as the left side, of the receiver 220 to signal a backtrack of the GUI 108 to change feature 1. This is one aspect of using wand directed movements for parameter selection and entry in the GUI 108. Similarly the user can hold the wand up, and direct the wand to the right side to skip over a parameter entry. Other wand gestures are disclosed ahead that can be applied, for example, to scroll through a menu of parameter entries, or paginate the workflow 110 forward or backward.

Figure 4A:
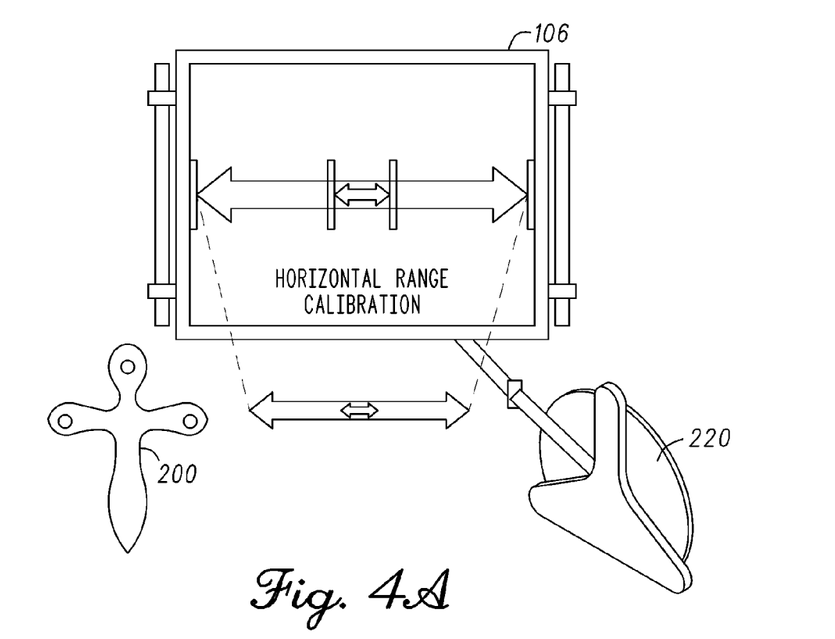
FIG. 4B is an exemplary illustration for horizontal workflow calibration in accordance with one embodiment.

At any time during method 300 or during the work-flow, the user can signal a user interface command to tune the wand 200 for calibration or a specific procedure. As one example, this can be achieved by moving the wand 200 towards the receiver 220 and pressing the button. A tuning page will permit the user to adjust a user interface setting (e.g., horizontal calibration, vertical calibration, zoom level, etc.) via one or more wand gestures (e.g., up/down, left/right, forward/backward, etc.). FIG. 4A illustrates an examples of horizontal range calibration. The navigation system 100 maps the horizontal range of the wand's motion to the display width; the mapping is a function of the wand 200 and receiver sensitivity which is based on the signal type (e.g., pulse, continuous), signal timing interval, the distance there between and the incident angle between the face of the wand 200 and receiver 220.

Figure 4B:
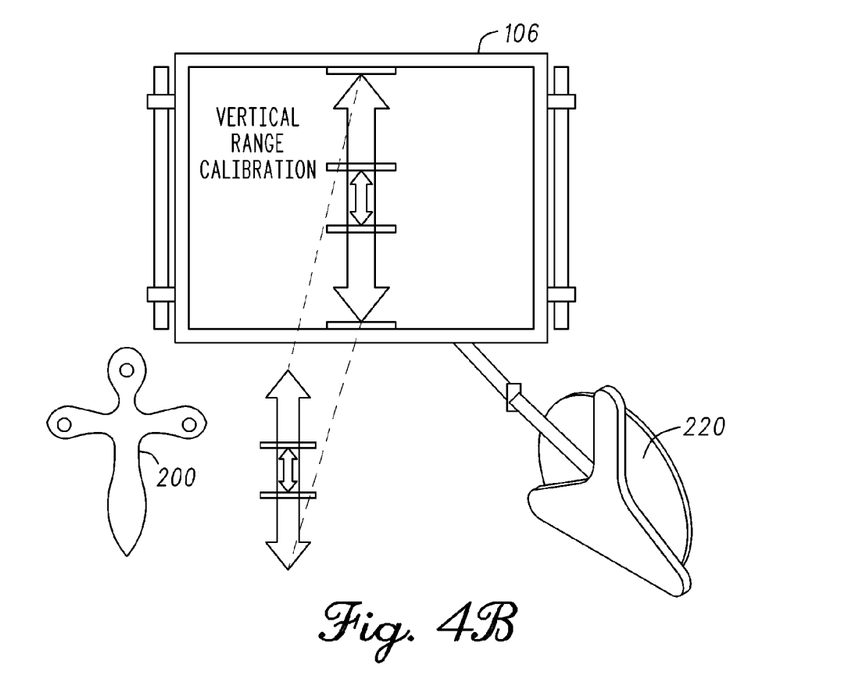

FIG. 4B illustrates an examples of vertical range calibration with similar tuning parameters as above. One example of touchless movement and range calibration enabled herein is disclosed in U.S. patent application Ser. No. 11/850,634; the entire contents of which are hereby incorporated by reference. Range calibration can also be controlled via wand movements. As an example, the user moves the wand 200 forward in proximity of the receiver 220 (<10 cm), holds it stationary, presses the button twice, or holds it down, until a visual acknowledgement is provided, then releases the button and proceeds to sweep it left and right and up or down depending on the page or workflow shown. The button may be pressed during range of motion to indicate an active calibration state.

Returning back to FIG. 3, at step 304, the navigation system 100 captures a first profile corresponding to a first touchless user interface movement of the wand 200 toward a first location, for instance, moving the wand to a right side. The first profile includes information about the wand's orientation and its positional movement along a time trajectory of its motion; for instance, as it moves from its current location to the right. The first profile can be generated locally on the receiver 220 upon the processing of received signals, or on the remote system 104 upon receipt of positional information or other directives. The first profile is stored to memory, preferably locally on the receiver 220, for comparative reference ahead.

Figure 5A:
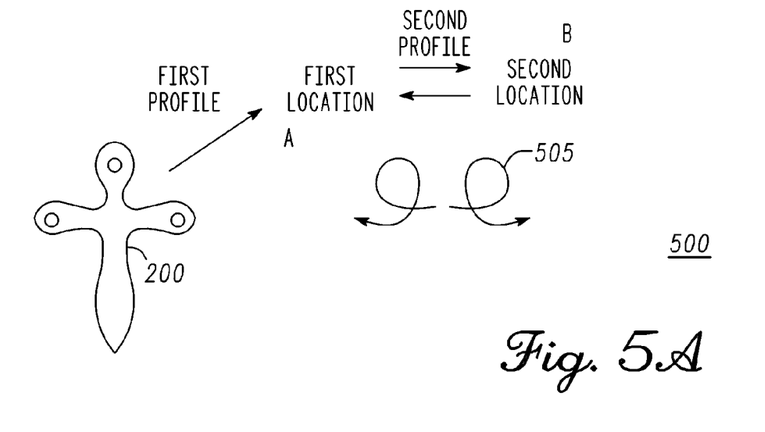
FIG. 5A is an exemplary illustration of a sequential wand command in accordance with one embodiment.

Briefly referring to FIG. 5A, an exemplary illustration of a directed wand movement to control the GUI 108 is shown in accordance with the method steps. As shown, the wand 200 is moved to a first location (A) on the right side during which time the first profile is captured. The first location can correspond to a predetermined location, such as an absolute (x, y, z) location or a relative location, such as a left, right, top or bottom side to the receiver 220 or display 106. The navigation system 100 tracks and saves the first profile of the wand movements during this directed movement in order to later track back along the history for recognizing wand gestures or directed user interface commands.

Returning back to FIG. 3, at step 306, the navigation system 100 captures a second profile of the wand movement (tracking a wand movement) directed away and back again to the first location. Briefly referring back to the illustration of FIG. 5A, this can be to a far-right of the receiver with respect to the first location, or to the immediate right with respect to a center first location. The second profile similarly includes information about the wand's orientation and its positional movement along a time trajectory during its motion; for instance, as it moves from the right side to the far-right and back again. Similarly, the second profile can be generated locally on the receiver 220 upon the processing of received signals, or on the remote system 104 upon receipt of positional information or other directives. When capturing the profile, the receiver 220 can identify any one of a continuous wand movement, an accelerated wand movement, a wand orientation and a stop wand movement. Moreover, it can capture any one of a plurality of profiles corresponding to wand movements or orientations before and between the capturing of the first profile and the second profile and thereafter.

At step 308, the navigation system 100 compares the first profile with the second profile while limiting a time window between the comparison. The comparison can include evaluating changes in location, orientation and acceleration as well as heuristic measures and state changes. The comparison includes evaluating differences in waveform properties, including time of flight information, amplitude and phase differences but is not limited to these. Examples of comparing profiles and waveforms used herein are disclosed in U.S. patent application Ser. Nos. 11/562,410 and 11/146,445 the entire contents of which are hereby incorporated by reference. The time window ensures that the movement is an intentional wand gesture completed within a predetermined amount of time.

User control wand movements directed away and back can be limited to less than half a second, though may be longer, whereas wand controlled registration of parameters of an identified feature can be one second or more. The later procedural registration allows for time averaging of the wand tip location. The comparison evaluates not only the differential characteristics of received signals but also relative direction, orientation and timing of the wand movements captured in the profile with respect to a state of workflow 110. Another example of comparing similarity of waveform profiles used herein is disclosed in U.S. patent application Ser. No. 11/562, 404 the entire contents of which are hereby incorporated by reference. Wand acceleration provides a further type of user control interaction wherein parameter entry and pagination is provided according to the wand's orientation and acceleration.

At step 310, the navigation system 100 activates a control of the work-flow 110 when the comparison of the first profile and the second profile correspond to a touchless command directive to the user interface occurring within the time window. A touchless command directive can be an intentional and sequential movement of the wand that is separate and distinct from the wand's normal movement used during the procedure. The command directive can derive from a continuous wand movement, an accelerated wand movement, a wand orientation and a stop wand movement. The navigation system 100 in response to the recognized command directive performs a user interface behavior according to the sequential combination thereof identified. One example of a sequential movement is shown in FIG. 5A, where the user intentionally moves the wand to a first location, pauses, and then directs the wand away and back to a second location. The second movement can be a back and forth wave or a pattern wave 505. Examples of touchless gestures and patterns for controlling a user interface used herein disclosed in U.S. patent application Ser. No. 11/930,014 and U.S. patent application Ser. No. 11/936,777 the entire contents of which are hereby incorporated by reference. Patterns include clockwise and counter-clockwise, front to back, and left to right, or other periodic spatio-temporal gestures.

The navigation system 100 permits directed control of the GUI 108 via wand 200 gestures, includes pagination control and parameter entry. As one example, shown in step 312, the GUI 108 can forward track a pagination from the current page to a next page when the comparison indicates the wand is directed and waved to one side, for instance, the right side. As shown in step 314, the navigation system 100 can backtrack pagination from the current page to a previous page when the comparison indicates the wand is directed and waved to another side, for instance, the left side. As shown in step 316, a workflow parameter can be entered in the GUI 108 responsive to wand movement.

Figure 5B:
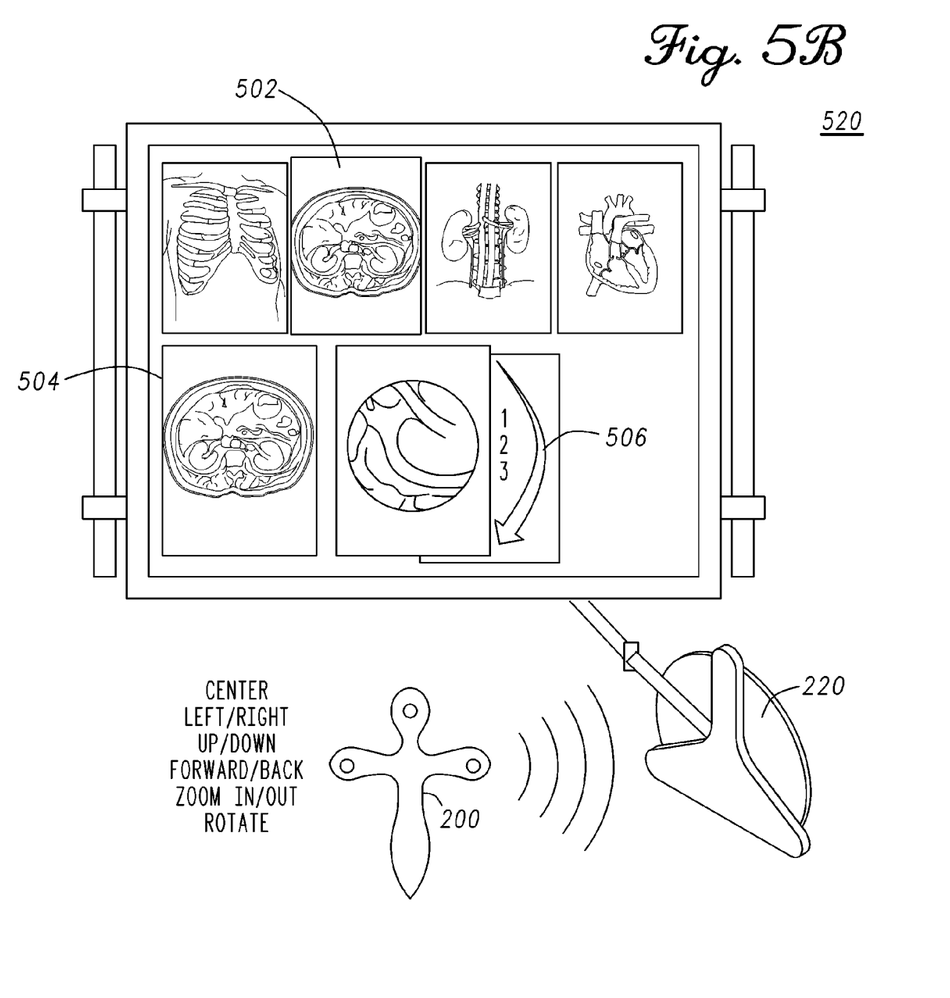
FIG. 5B is an exemplary illustration of a user interface display in accordance with one embodiment.

Referring to FIG. 5B, various wand gestures for controlling the GUI 108 and paginating the workflow 110 are shown, and include left/right, up/down, forward backward, pauses, accelerated, jitter, and twist movements and combinations thereof. Examples of detecting such gestures and patterns are described in U.S. patent application Ser. No. 11/566,137 the entire contents of which are hereby incorporated by reference. As one example, the user can slightly twist the wand 100 along a local axis (x, y, z) to scroll through a thumbnail list 502, decline an entry, or close a parameter entry list. As another example, the user can tilt the wand forward and backward to select an entry, accept a prompt, mark a label 504, or tilt the wand left and right to rotate an image 506. As another example, a wand gesture can reset a page, for example, allowing the user to start anew on parameter entry or a certain aspect of a navigated procedure.

As previously indicated the user can motion the wand away and back again from a certain location where the direction and location determines the user action, for example, forward tracking or back tracking. As another example, the user hold the wand outside a predetermined area associated with the workflow procedure (e.g., surgical site), press the button and move forward and backward to zoom in or out of the GUI. The wand can then resume its navigational tool use on re-entry of the predetermined area. The area can be a procedure area (e.g., 20 in sq. volume), an area proximal to the receiver 220 (eg. 10 cm sq. volume), a virtual area in front of the display (e.g., a quadrant) or a region beyond the display (e.g., top, bottom, left, right). One example of touchless control enabled herein is disclosed in U.S. patent application Ser. No. 11/844, 329; the entire contents of which are hereby incorporated by reference.

Upon reviewing the aforementioned embodiments, it would be evident to an artisan with ordinary skill in the art that said embodiments can be modified, reduced, or enhanced without departing from the scope and spirit of the claims described below. For example, the receiver by way of accelerometer measurements can create a femur vector from the determined pivot point to a registered knee center, and a tibial wand can be used to create one or more tibia vectors on the tibia by accelerometer measurements alone rather than manually using the wand to register the ankle center. The wand can be affixed to the mid tibia to capture tibia orientation and generate the tibia vectors. Similarly the receiver can be attached to the distal femur to capture its orientation and generate the femur vectors relative to the determined pivot point. A second wand in communication with the affixed receiver can then be used to virtually connect the tibia vectors and the femur vectors at the knee center to assess overall alignment. Furthermore, this second wand can be coupled to a cutting jig for orienting the cutting jig for directing cuts on the distal femur and proximal tibia according to a desired alignment and workflow procedure.

While the preferred embodiments of the invention have been illustrated and described, it will be clear that the embodiments of the invention are not so limited. Numerous modifications, changes, variations, substitutions and equivalents will occur to those skilled in the art without departing from the spirit and scope of the present embodiments of the invention as defined by the appended claims.

What is claimed is:

1. A navigation system for directing a touchless control action, the system comprising:
   a user interface that displays an interactive work-flow;
   a sensing unit for controlling a pagination and parameter entry of the work-flow responsive to tracking a wand movement and capturing a first profile signal corresponding to the wand movement directed to a first location, and ultrasonically capturing a location or position of a muscular skeletal system;
   a processor communicatively coupled to the sensing unit for comparing the first profile signal with a second profile signal captured during wand movement to a second location, the second profile signal corresponding to the wand movement directed away and back again to the first location, where the captured first profile signal and the second profile signal are either emitted from or reflected from the wand;
   a clock for limiting a time window between the comparing of the first profile signal and the second profile signal, and
   a controller communicatively coupled to the device for activating a user interface control in the work-flow when the comparison of the first profile signal and the second profile signal corresponds to a touchless command directive to the user interface.

2. The navigation system of claim 1, wherein the processor:
   backtracks pagination from a current page to a previous page when the comparison indicates the wand is directed and waved to a first side, and forwards pagination from a current page to a next page when the comparison indicates the wand is directed and waved to a second side.

3. The navigation system of claim 1, wherein the sensing unit detects a continuous wand movement, an accelerated wand movement, a pattern wand movement, a wand orientation and a stop wand movement and controls the user interface according to a sequential combination thereof.

4. The navigation system of claim 1, wherein the sensing unit captures at least one of a plurality of profiles signals corresponding to wand movements between the capturing of the first profile signal and the second profile signal, and saves at least one of the plurality of profiles signals to memory for comparative reference.

5. The navigation system of claim 1, wherein the sensing device consists of an active element that comprises at least one of an ultrasonic transmitter, an optical transmitter, an infrared transmitter, and a laser.

6. The navigation system of claim 1, where the sensing unit comprises:
- a wand including:
  - a plurality of transmitters to transmit positional signals;
  - a communication port to receive timing directives to transmit the signals;
  - an interface to receive user input on the wand; and
- a receiver including:
  - a plurality of sensors to receive the signals transmitted by the wand;
  - a processor to resolve from the received signals received wand movement;
  - a communications interface to transmit the timing directives to the wand and convey the wand movement to a remote system.

7. The navigation system of claim 6, wherein the receiver includes
a memory for saving at least one profile of the user interface movements of the wand; wherein at least one profile further includes coordinate information comprising a relative displacement, orientation and location of the wand.

8. The navigation system of claim 6, wherein the wand includes an accelerometer to indicate an orientation of the wand, and the processor provides the parameter entry according to the orientation and acceleration of the wand.

9. The navigation system of claim 6, further comprising the remote system, wherein the remote device is a computer, laptop or display that exhibits a visual acknowledgement of the wand movement.

10. The method of claim 6, wherein the wand interface comprises a navigation press button to complement control of the user interface.

11. A navigation system for directing a touchless control action, the system comprising:
- a user interface that displays an interactive work-flow;
- a sensing unit for controlling a pagination and parameter entry of the work-flow responsive to tracking a wand movement and capturing a first profile signal corresponding to the wand movement directed to a first location;
- a processor communicatively coupled to the sensing unit for comparing the first profile signal with a second profile signal captured during wand movement to a second location, the second profile signal corresponding to the wand movement directed away and back again to the first location;
- a clock for limiting a time window between the comparing of the first profile signal and the second profile signal, and
- a controller communicatively coupled to the device for activating a user interface control in the work-flow when the comparison of the first profile signal and the second profile signal corresponds to a touchless command directive to the user interface,
where the sensing unit comprises:
a wand including:
  - a plurality of transmitters to transmit positional signals;
  - a communication port to receive timing directives to transmit the signals;
  - an interface to receive user input on the wand; and
a receiver including:
  - a plurality of sensors to receive the signals transmitted by the wand;
  - a processor to resolve from the received signals received wand movement;
  - a communications interface to transmit the timing directives to the wand and convey the wand movement to a remote system and where the wand and the receiver are instruments that register anatomical points of interest and report anatomical alignment and positional measurements of the registered points during a procedure while intermittently used for touchless user interface control.

12. A method for virtual navigation of a user interface workflow, the method comprising the steps of:
- tracking a wand movement and capturing a first profile signal corresponding to the wand movement directed to a first location;
- tracking the wand movement to a second location and capturing a second profile signal corresponding to the wand movement directed away to the second location and back again to the first location;
- comparing the first profile signal with the second profile signal while limiting a time window between the comparison of the first profile signal and the second profile signal; and
- activating a behavior in the work-flow when the comparison of the first profile signal and the second profile signal corresponds to a touchless command directive to the user interface, where the captured first profile signal and the captured second profile signal are either emitted from or reflected from the wand, and where the wand is an instrument that registers anatomical points of interest and reports anatomical alignment and positional measurements of the registered points during a procedure.

13. The navigation system of claim 12, wherein the processor:
backtracks pagination from a current page to a previous page when the comparison indicates the wand is directed and waved to a first side, and forwards pagination from a current page to a next page when the comparison indicates the wand is directed and waved to a second side.

14. The method of claim 12, comprising:
identifying one of a continuous wand movement, an accelerated wand movement, a wand orientation and a stop wand movement; and,
performing the behavior according to a sequential combination thereof.

15. The method of claim 12, comprising:
capturing at least one of a plurality profile signals corresponding to a plurality of wand movements between the capturing of the first profile signal and the second profile signal, and
saving at least one of the plurality of profiles signals to memory for comparative reference.

16. The method of claim 12, comprising controlling the pagination or parameter entry via a button press on the wand.

17. A remote system for virtual navigation, the remote system comprising:
a processor;
a power supply for powering the processor a user interface to display an interactive work-flow by way of the processor; and
a communications interface communicatively coupled to the processor that receives from a sensing unit information for controlling a pagination and parameter entry of the work-flow, where the sensing unit:
tracks a first touchless user interface movement of a wand directed to a first location in the user interface, captures a first profile signal corresponding to the first touchless user interface movement at the first location;

compares the first profile signal with a second profile signal captured during touchless user interface tracking of the wand to a second location of the user interface and back to the first location, the second profile signal corresponding to a second touchless user interface movement directing the wand away and back again to the first location;

limits a time window between the comparing of the first profile signal and the second profile signal, and activates a behavior in the work-flow when the comparison corresponds to a touchless command directive to the user interface, and where the captured first profile signal and the captured second profile signal are either emitted from or reflected from the wand, and where the wand is an instrument that registers anatomical points of interest and reports anatomical alignment and positional measurements of the registered points during a procedure.

18. The remote system of claim 17, where the user interface:

backtracks pagination from a current page to a previous page when the comparison indicates the wand is directed and waved to a first side, and forwards pagination from a current page to a next page when the comparison indicates the wand is directed and waved to a second side.

19. The remote system of claim 17, includes a memory for saving at least one profile signal of the user interface movements of the wand, wherein at least one profile further includes coordinate information comprising at least one of a relative displacement or position of the wand.

20. The remote system of claim 17, wherein the remote system identifies at least one of a continuous wand movement, an accelerated wand movement, a wand orientation, and a stop wand movement and performs the behavior to a sequential combination thereof.

21. A navigation system for a touchless control action in an orthopedic application, the system comprising:

a user interface that displays an interactive work-flow of a surgical procedure;

a sensing unit for controlling a pagination and parameter entry of the work-flow responsive to tracking a wand movement within a sterile field, capturing a first profile corresponding to the wand movement directed to the first location, and ultrasonically capturing a location or position of the muscular-skeletal system;

a processor communicatively coupled to the sensing unit for comparing the first profile with a second profile captured during wand movement to a second location, the second profile corresponding to the wand movement directed away and back again to the first location;

a clock for limiting a time window between the comparing of the first profile and the second profile, and a controller communicatively coupled to the device for activating a user interface control in the work-flow when the comparison of the first profile and the second profile corresponds to a touchless command directive to the user interface.

* * * * *